United States Patent
Christiansen

(10) Patent No.: US 8,211,055 B2
(45) Date of Patent: Jul. 3, 2012

(54) DRUG ELUTING BALLOON

(75) Inventor: Frank K. Christiansen, Haslev (DK)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 12/677,050

(22) PCT Filed: Sep. 11, 2008

(86) PCT No.: PCT/US2008/075944
§ 371 (c)(1),
(2), (4) Date: Oct. 15, 2010

(87) PCT Pub. No.: WO2009/036118
PCT Pub. Date: Mar. 19, 2009

(65) Prior Publication Data
US 2011/0060275 A1      Mar. 10, 2011

Related U.S. Application Data

(60) Provisional application No. 60/993,361, filed on Sep. 12, 2007.

(51) Int. Cl.
*A61M 29/00*        (2006.01)

(52) U.S. Cl. .................................................. 604/101.02
(58) Field of Classification Search ............. 604/101.02
See application file for complete search history.

(56) References Cited

U.S. PATENT DOCUMENTS

| | | | |
|---|---|---|---|
| 6,733,474 B2 * | 5/2004 | Kusleika .................. | 604/103.01 |
| 7,074,233 B1 * | 7/2006 | Gowda et al. ................... | 607/89 |
| 2002/0077564 A1 * | 6/2002 | Campbell et al. ............. | 600/549 |
| 2002/0115982 A1 * | 8/2002 | Barbut et al. ................. | 604/509 |
| 2008/0319415 A1 * | 12/2008 | Shturman ..................... | 604/509 |
| 2010/0121308 A1 * | 5/2010 | Muni et al. .................... | 604/514 |

* cited by examiner

*Primary Examiner* — Nicholas Lucchesi
*Assistant Examiner* — Jason Flick
(74) *Attorney, Agent, or Firm* — Brinks Hofer Gilson & Lione

(57) ABSTRACT

There is disclosed a drug eluting balloon catheter assembly provided with a balloon formed of an inner balloon member of non-compliant material and an outer balloon member of a compliant material and which is provided with holes therein for eluting a drug or other fluid. In use, the outer balloon member is biased by contraction onto the inner balloon member thereby keeping the holes therein normally sealed closed and minimizing dead space in the device.

16 Claims, 3 Drawing Sheets

DRUG ELUTING BALLOON

CROSS-REFERENCE TO RELATED APPLICATIONS

This application is a U.S. nationalization of PCT application No. PCT/US2008/075944, filed Sep. 11, 2008, and claims priority to U.S. Provisional Application Ser. No. 60/993,361, filed Sep. 12, 2007.

FIELD OF THE INVENTION

The present invention relates to a human or veterinary medical device and, more particularly, to a balloon designed to elute a drug, bioactive agent, therapeutic agent or diagnostic agent. The present invention also relates to a catheter assembly including such a balloon.

BACKGROUND OF THE INVENTION

It has become common to treat a variety of medical conditions by temporarily or permanently introducing a coated medical device, and, in particular, a coated medical implanted device partly or completely into the esophagus, trachea, colon, biliary tract, urinary tract, vascular system or other location within a human or veterinary patient. Many treatments of the vascular or other systems entail the introduction of a device such as a stent, a catheter, a balloon, a wire guide, a cannula or the like. For this purpose, a stent may most simply be considered as a cylinder of relatively short length which opens a body passage or lumen or which maintains a body passage or lumen in an open condition. In addition, balloons such as angioplasty or dilation balloons may be advanced into the human or veterinary patient and then expanded to open the body passage or vessel lumen.

Such medical devices are generally capable of serving their intended purposes quite well. Some drawbacks can be encountered during their use, however. For example, when a balloon is expanded to open a body passage or vessel lumen, the expanded balloon may cause potential trauma or injury to the expanded passage or vessel. Likewise, when a device is introduced into and manipulated through the vascular system of a patient, the blood vessel walls can be disturbed or injured. Clot formation or thrombosis often results at the injured site, causing stenosis (closure) of the blood vessel. Moreover, if the medical device is left within the patient for an extended period of time, thrombus can form on the device itself, again causing stenosis. As a result, the patient is placed at risk of a variety of complications, including heart attack, pulmonary embolism, and stroke. Thus, the use of such a medical device can entail the risk of precisely the problems that its use was intended to ameliorate.

When medical devices such as stents and, in particular, coated stents are implanted in a vessel lumen, edge effect trauma can occur to the tissue at and beyond the ends of the implanted stent. This trauma or injury can be the result of the implanted stent causing injury to the vessel wall. However, delivery of such an implanted stent normally includes the use of an inflatable balloon on which the stent is mounted with the ends of the balloon extending axially beyond the ends of the stent. When the balloon is inflated to deliver the stent, the ends of the balloon extending beyond that of the stent inflate so as to dilate and injure the tissue extending beyond the ends of the stent. Should the stent be coated or include a therapeutic agent, the therapeutic agent can possibly cause injury to the tissue extending beyond the ends of the stent. This therapeutic agent or treatment could include a chemical, radiation, or biochemical agent or other type of treatment. Furthermore, delivery agents such as polymers and the like used to deliver the treatment agent can also cause this edge effect reaction to the tissue extending beyond the ends of the implanted stent. However, it is to be understood that regardless of the cause of the trauma or injury to the vessel wall, the tissue will typically react with the proliferation of smooth muscle cells and the like, thereby creating an adverse reaction and subsequent closure or stenosis of the vessel.

Another way in which blood vessels undergo stenosis is through disease. Probably the most common disease causing stenosis of blood vessels is atherosclerosis. Many medical devices and therapeutic methods are known for the treatment of atherosclerotic disease.

Several conditions and diseases are now treatable with stents, catheters, cannulae and other medical devices inserted into the esophagus, trachea, colon, biliary tract, urinary tract and other locations in the body. A wide variety of bioactive materials (drugs, therapeutic agents, diagnostic agents and other materials having biological or pharmacological activity within a patient) have been applied to such medical devices for the purpose of introducing such materials into the patient. Unfortunately, the durable application of bioactive materials to stents and the like, sufficient for such introduction to successfully occur, is often problematic. Moreover, as explained above, the stent itself can cause trauma to the vessel walls, leading in some cases to thrombosis or restenosis.

As an alternative or addition to the use of drug coated or otherwise eluting stents, it is known to use balloon catheters with either a drug coated balloon or with a double balloon structure in which an outer layer is provided with a series of holes through which a drug can pass from an internal chamber of the balloon. The advantage of such drug eluting balloons is that a balloon structure can in some instances cause less trauma to the site being treated and is a temporary mechanism for delivering drugs.

US Publication No. 2003/0032851, for example, discloses a balloon catheter assembly which includes a balloon formed of two layers of non-compliant material which form a chamber for a drug therebetween. The outer balloon is made of a non-compliant material so as to conform to the vessel wall at the treatment site. The catheter element of the assembly includes a lumen for supplying a drug to the chamber formed between the balloon layers.

US Publication No. 2002/0042593 discloses a catheter system having a bulbous or inflatable drug eluting end provided with an outer wall or layer, the outer layer having a series of apertures formed therein. The bulbous end is provided with a bolus of treatment material therein, which can be discharged from the catheter assembly by operation of a pumping mechanism. In one embodiment of the inflatable balloon device disclosed in this document, the cavity within the outer layer of the balloon is loaded with a drug in the uninflated state, and as the balloon is inflated, the drug is discharged through apertures in the outer layer as the inner layer is expanded into the space previously filled with drug.

The above-mentioned devices, while avoiding the use of an implantable device such as a stent for delivery of a medicament, can suffer some disadvantages. For instance, the provision of a chamber within the balloon or other bulbous structure has a size necessarily restricted to the amount of drug to be delivered at least in the first instance during inflation of the balloon. Moreover, the apertures in the outer layer provide an escape path for blood, which must therefore be closed by a suitable valving system, typically provided at a location on the catheter assembly remote from the balloon or other bulbous member. This inevitably results in some blood loss and collection in the catheter assembly.

SUMMARY OF THE INVENTION

According to an aspect of the present invention, there is provided a medical balloon assembly for administration of treatment material to a vessel or organ of a patient including inner and outer balloon members, the inner balloon member being located within the outer balloon member so as to be enveloped thereby, the outer balloon member being more compliant than the inner balloon member and being of a size so as to be in a stretched condition when the inner balloon member is inflated, the outer balloon member allowing the passage of fluids therethrough.

In this connection, the outer balloon member could be provided with one or more holes or ports therein for elution of medicament. In another embodiment, the outer balloon member could be formed of a porous material. It is also envisaged that the outer balloon member can be formed of a porous material which also has formed therein one or more holes or ports.

It is to be understood that the outer balloon member need not be of a type which is able to hold an inflated condition as its expansion will be determined by the expansion of the inner balloon member.

Advantageously, the outer balloon member is of a size such that it is also biased towards the inner balloon member when the inner balloon member is in an uninflated state.

In the preferred embodiment, the outer balloon member is in a stretched condition both when the inner balloon member is uninflated or partially inflated and when it is inflated. This provides for little or virtually no dead space between the inner and outer balloon members in all operating states of the balloon. Moreover, upon the introduction of a medicament between the two balloon members, the tendency of the outer balloon member to contract onto the inner balloon member will cause the outer balloon member to elute the medicament without the need for any other pumping system.

Furthermore, this natural contracting tendency will in practice close off any passage through the balloon structure, thus avoiding blood loss through the balloon assembly and avoiding the need for a separate valving system to close off any such escape route. More particularly, as the outer balloon member is made of a compliant material, when this is stretched over the inner balloon, the holes or porous passages will be closed against the inner balloon member, thereby providing an automatic valving feature.

It is considered that there is no practical lower limit to the required differences in compliances between the inner and outer balloon members for the device to work as desired, although it is considered preferable to have a difference in compliances of at least 25% between the inner and outer balloon members, and in some embodiments 50% or more. In general terms, there is no upper limit to these differences either as the inner balloon member could be made of a non-compliant material and the outer member of a very compliant material, as long as the outer balloon member retains the ability to contract onto the inner balloon member when it is stretched.

In some embodiments, the outer balloon member could be made of a rubber or rubberised material, silicone, polyurethane or a thermoplastic elastomer. Any compliable biocompatible material could be used.

It is envisaged that the inner balloon member could be formed of the same material as the outer balloon member, whereby the difference in compliances could be achieved by making the inner balloon member thicker than the outer balloon member.

In other embodiments, the inner balloon member could be made of a different material, particularly in the case where it is desired that the inner balloon member be made of a substantially non-complaint material. In this case, the inner balloon member could be made of PET (polyethylene terephthalate), polyethylene, Nylon, polyamide polymer, or any other material commonly used for non-compliant balloons for medical applications.

Thus, advantageously, the inner balloon member is formed of a substantially non-compliant material, thereby to be able to be sized in accordance with the dimensions of the vessel into which the assembly is to be deployed.

There may be provided a coating on the outer balloon member in order to improve its slip properties. Any suitable slip coating, hydrophilic coating, nano coating could be used including a coating of polyurethane of elastomeric rubber approved for medical applications.

In the preferred embodiment, there is provided a plurality of holes in the outer balloon member. These may be arranged substantially symmetrically around the outer balloon member. However, in other embodiments, the holes could be provided in a predetermined pattern, advantageously so as to apply medicament to a specific area of a patient, for example only to one side or zone of the interior wall of a vessel.

The holes may differ in size. For example, the holes may be smaller at a proximal end of the balloon assembly, that is at an end of the balloon that is closer to the external manipulation end of the catheter assembly.

The balloon assembly may be provided with one or more radio-opaque markers.

One or both of the balloon members may be multi-layered.

Advantageously, the outer balloon member may have a greater wall thickness at its proximal end relative to its distal end.

According to another aspect of the present invention, there is provided a balloon catheter assembly including a balloon assembly as herein specified and a catheter element including a first lumen through which balloon inflation fluid can be supplied to the inner balloon member and a second lumen through which a treatment fluid can be supplied between the inner and outer balloon members.

According to another aspect of the present invention, there is provided a method of treating a patient including the steps of providing a balloon catheter assembly including a balloon assembly as herein specified, inflating the inner balloon member by passing an inflation fluid through the inflation lumen, passing a treatment fluid through the delivery lumen to between the inner and outer balloon members, thereby to cause said treatment fluid to open holes in the outer balloon member and to allow said treatment fluid to elute from the balloon assembly.

The embodiments taught herein can provide devices and methods for reliably delivering suitable therapeutic and diagnostic agents, drugs and other bioactive materials directly into a body portion during or following a medical procedure, so as to treat or prevent a variety of conditions and diseases, for example, to prevent abrupt closure and/or restenosis of a body portion such as a passage, lumen or blood vessel. They can also limit systemic exposure of the patient to such bioactive materials. This can be particularly advantageous in therapies involving the delivery of a chemotherapeutic agent to a particular organ or site through an intravenous catheter (which itself has the advantage of reducing the amount of agent needed for successful treatment), by preventing stenosis both along the catheter and at the catheter tip. They can also be used to improve other therapies. They can also deliver material to a treatment site of a patient without causing additional problems with a poor biocompatible carrier or containment material.

The preferred embodiments are also able to minimize and preferably eliminate edge effects that can ultimately cause trauma to the vessel wall and subsequent occlusion or stenosis of the vessel.

DESCRIPTION OF THE PREFERRED EMBODIMENTS

Figure 1:
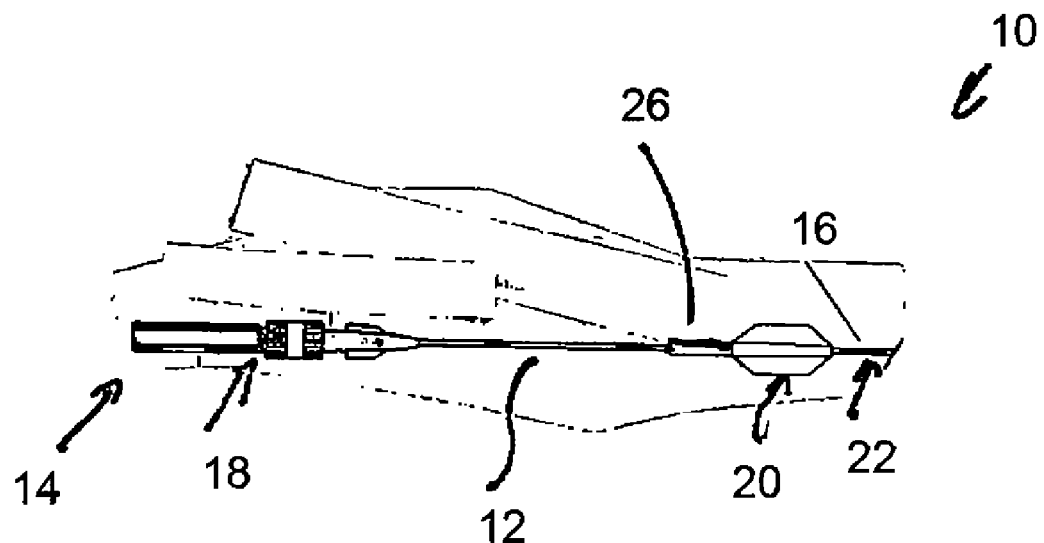
FIG. 1 shows in schematic form an embodiment of balloon catheter assembly.

Referring to FIG. 1, there is shown in schematic form an example of balloon catheter assembly 10. The assembly includes an elongate catheter 12 of such a length that the proximal end 14 of the assembly 10 remains outside the patient even when the distal end 16 is at the treatment site within the patient.

The proximal end 14 is provided with external manipulation elements 18 of a type well known in the art, including one or more handles for use by the surgeon in moving and placing the catheter, connectors for connecting the catheter to a source of medicaments or other fluids, balloon inflation equipment and so on. The proximal end also includes a connector port for the passage of a guide wire therethrough as well as other elements conventionally found in such assemblies.

At or adjacent the distal end of the assembly 10 there is provided an inflatable balloon assembly 20, described in further detail below. At the tip of the distal end 16, there is advantageously provided a radio opaque marker 22 of known type.

Figure 2:
FIG. 2 shows in schematic form in cross-section an embodiment of catheter assembly showing the inflation and medicament lumens.

Referring now to FIG. 2, there is shown in enlarged form a transverse cross-sectional view of an embodiment of catheter 12.

The catheter 12 is provided with a guide wire lumen 24 for the passage of a guide wire therethrough. This lumen 24 extends for the whole length of the catheter 12 such that a guide wire can extend beyond the distal end 22 of the lumen. Typically, the lumen 24 also extends to beyond the proximal end 14 of the catheter 12 so that the guide wire may be manipulated from the proximal end. In the case of a rapid exchange or short wire catheter assembly, the guide wire lumen 24 may only extend through the distal portion of the catheter 12. In particular, the wire guide lumen 24 may extend between a distal wire guide port at the distal end 16 of the assembly 10 and a proximal wire guide port formed at an intermediate location 26 spaced a substantial distance distal of the proximal end 14 of the assembly 10, in a manner known in the art. In some embodiments, the proximal wire guide port may be located proximate the balloon 20.

The catheter also includes an inflation lumen 28 for inflating the balloon assembly 20, as described in further detail below, which extends from the proximal end of the catheter assembly 10 to the balloon assembly 20. Typically, the inflation lumen 28 is coupled through the external manipulation section 18 to an inflation device of known form.

The third lumen 29 extends from the external manipulation section 18 to the balloon assembly 20, and in particular to a cavity between inner and outer layers of the balloon assembly, as described in more detail below. This third lumen 29 is in use coupled to a source of a drug, a bioactive agent, a therapeutic agent or a diagnostic agent, in a known manner.

Figure 3:
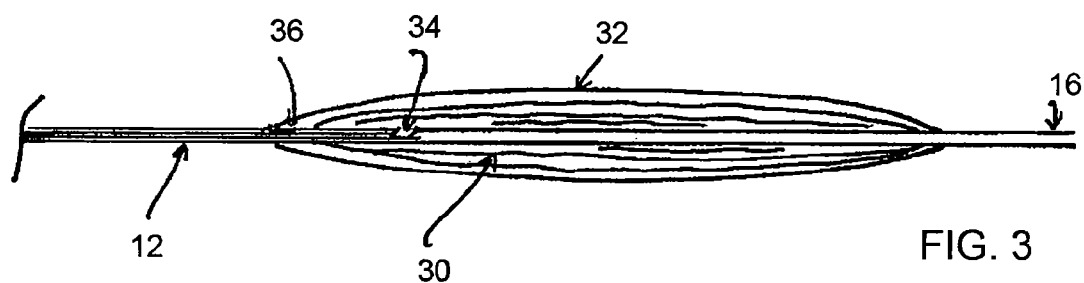
FIG. 3 shows in schematic form a preferred embodiment of balloon assembly in an uninflated state.
Figure 4:
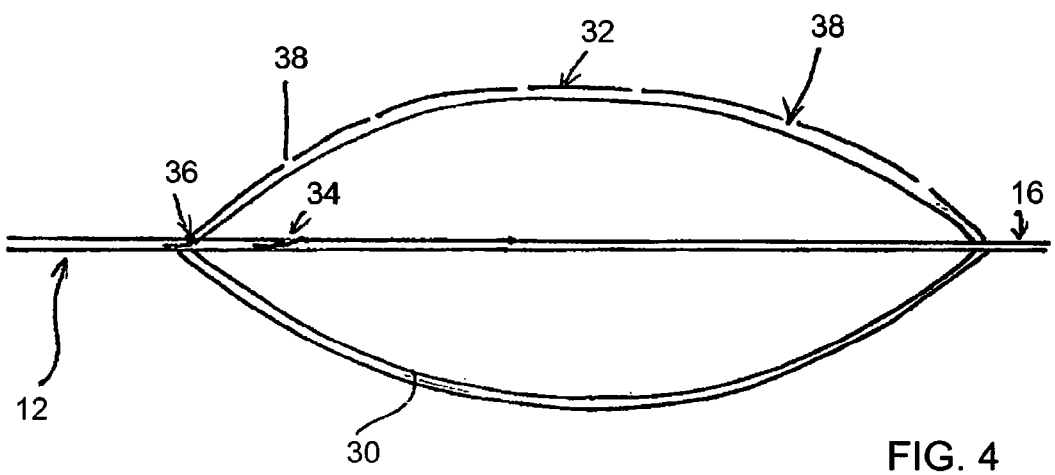
FIG. 4 shows in schematic form the balloon assembly of FIG. 2 in an inflated state.
Figure 5:
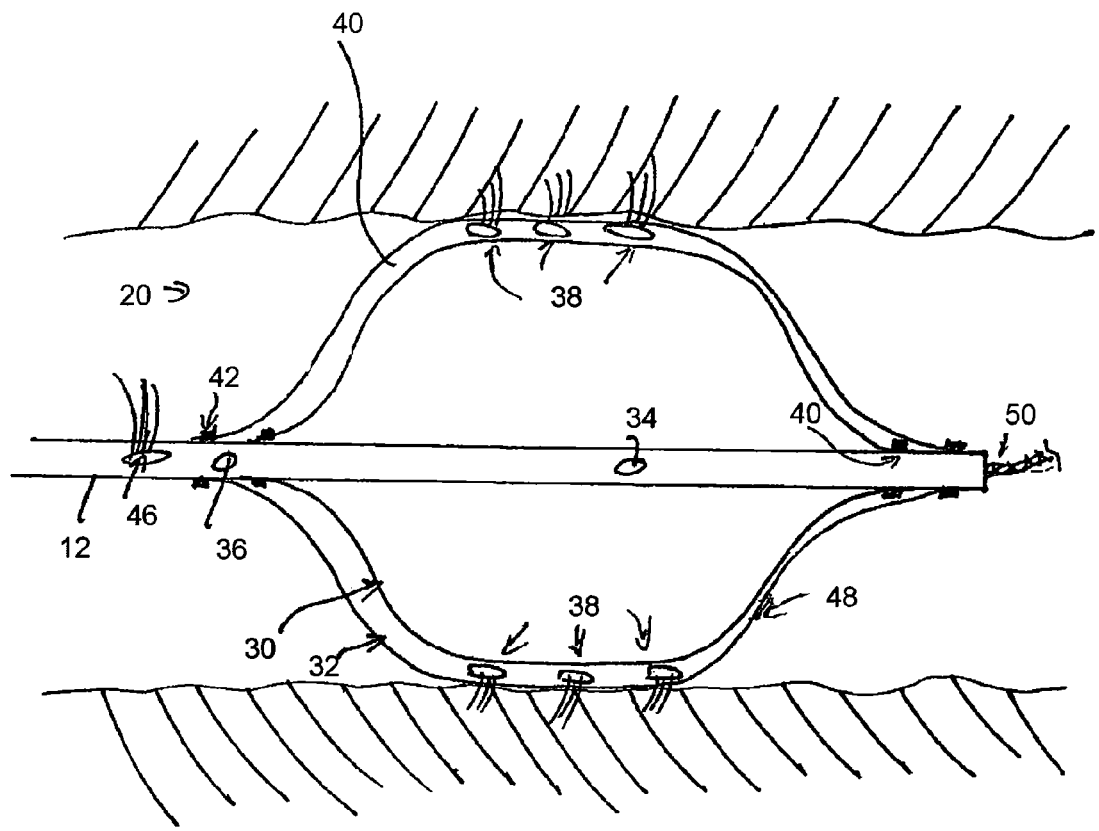
FIG. 5 shows in schematic form the balloon assembly of FIGS. 2 to 4 in situ in the vasculature of a patient.

Reference is now made to FIGS. 3 to 5 which show a preferred embodiment of the balloon assembly 10. These Figures are not scale drawings and have been drawn to emphasise the features disclosed herein.

Referring now to FIG. 3, there is shown in schematic form and in longitudinal cross-section a view of the preferred embodiment of balloon assembly 20 in a deflated condition. The balloon 20 is formed of inner and outer balloon members 30 and 32, respectively. The outer balloon member 32 overlies the inner balloon 30 so as to envelop it entirely, although in some embodiments it could overlie only a portion of the inner balloon 30 and be fixed thereto. The outer balloon 32 is fixed to the catheter 12 in any suitable manner.

The inner balloon 30, as illustrated in FIG. 3, is also fixed to the catheter 12 in any known or otherwise suitable manner, and is shown in an uninflated condition. When in the uninflated condition, the inner balloon 30 would typically be folded over itself so as to form a plurality of pleats in the longitudinal direction of the catheter 12 for storage and delivery purposes. FIG. 3 also shows a port 34 which is coupled to or in fluid communication with the inflation lumen 28 of the catheter 12. A port 36 is similarly coupled to the delivery lumen 29.

The inner balloon member is preferably made from a non-compliant material such as made of PET (polyethylene terephthalate), polyethylene, Nylon, polyamide polymer, polyurethane or any other material commonly used for non-compliant balloons for medical applications.

The outer balloon member 32 is made from a compliant material such as a rubber or rubberised material, silicone, polyurethane or a thermoplastic elastomer. Any compliable biocompatible material could be used.

It is envisaged that the inner balloon member could be formed of the same material as the outer balloon member and in such an event the difference in compliances could be achieved by making the inner balloon member thicker than the outer balloon member.

It is considered that there is no practical lower limit to the required differences in compliances between the inner and outer balloon members for the device to work as desired, although it is considered preferable to have a difference in compliances of at least 25% between the inner and outer balloon members, and in some embodiments 50% or more. In general terms, there is no upper limit to these differences either, as the inner balloon member could be made of a non-compliant material and the outer member of a very compliant material, as long as the outer balloon member retains the ability to contract onto the inner balloon member when it is stretched.

There may be provided a coating on the outer balloon member in order to improve its slip properties, i.e., to reduce any frictional forces that may be generated as the assembly 10 is advanced into the patient. Any suitable slip coating, hydrophilic coating, nano coating could be used including a coating of polyurethane of elastomeric rubber approved for medical applications.

The outer balloon member 32 is preferably of a material and size such that when the inner balloon 30 is in an uninflated state, as shown in FIG. 3, the outer balloon 32 contracts so as to lie closely against the inner balloon 30. In other words, the non-stretched inner diameter of the outer balloon 32, at least in some embodiments, is less than the re-wrapped (folded and/or pleated) diameter of the inner balloon member 30, such that when fitted over the inner balloon member 30 the outer balloon member 32 is always stretched. The outer balloon member 32 is also of a material and form which is able to stretch on inflation of the inner balloon 30 so as to follow the form of the inner balloon, as shown in FIG. 4.

As can be seen in particular in FIG. 4, the outer balloon member 32 is provided with a plurality of holes 38 therein for eluting a medicament or other treatment compound (typically a fluid), as described below in further detail in connection with FIG. 5. FIG. 4 shows holes 38 on one side only of the outer balloon member 32, in which case medicament or treatment compound would be discharged or eluted in only one radial direction of the balloon assembly 20. In other embodiments, there may be holes 38 provided circumferentially around the entirety of the outer balloon member 32, in which case the outer balloon member 32 would be suitable for eluting compound around its entire circumference. The arrangement, number and sizes of the holes 38 can be chosen as desired depending on the type of treatment to be performed.

Although FIG. 4 shows the outer balloon member 32 being spaced from the inner balloon member 30, it should be understood that the outer balloon member 32 is stretched over and in substantial contact with the inner balloon member 30 when the inner balloon member 30 is in the inflated or expanded state. Nevertheless, portions of the outer balloon member 2 may be spaced away from the inner balloon member 30 by the passage of a treatment fluid there between, as will be explained below. When the inner balloon member 30 is in the uninflated or collapsed state, as illustrated in FIG. 3, the outer balloon member 32 likewise preferably is stretched over and in substantial contact with the inner balloon member 30 so as to reduce the overall profile of the assembly 10 for delivery into the patient.

When the outer balloon member 32 is stretched over the inner balloon member 30, it is substantially in complete contact therewith. In other words, the edges of outer balloon member 32 which define the holes 38 touch or engage the inner balloon member 30 with no space between the inner and outer balloon members 30, 32. This has the effect of sealing or closing the holes 38, which consequently seals or closes the passage to the delivery lumen 29 of the catheter 12. Thus, there is no need to have any other valving device for stopping the passage and escape of bodily fluids through the holes 38 and into the delivery lumen 29.

Referring now to FIG. 5, there is shown an enlarged view, in cross-section, of the preferred embodiment of balloon assembly 20 in situ in an artery of a patient and loaded with a treatment compound.

As can be seen, the balloon assembly 20 has been inflated such that the inner and outer balloon members 30 and 32 are in an inflated or expanded condition, with the outer balloon member 32 abutting the vascular wall. Treatment fluid, for example a drug, is shown being pumped through the delivery lumen 29 into the interstitial space between the inner and outer balloon members 30, 32. As the fluid is pumped in this manner, it flows between the inner and outer balloon members 30, 32, in effect creating a space 40 therebetween, achieved by the stretchability of the outer balloon member 32. The drug is supplied at the required location in the patient through the holes 38, with little wastage.

Once the flow of drug of other fluid into the balloon assembly 20 is stopped, the resiliency of the material of the outer balloon member 32 causes it to contract back onto the inner balloon 30, in so doing eluting any remaining drug between these two and causing the holes 38 to become sealed again.

At the end of the procedure, inflation pressure to the inner balloon is removed, in which case the inner balloon 30 can collapse again. In the preferred embodiment, the outer balloon has a natural non-stretched state which is smaller than the inflated size of the inner balloon 30 and most preferably only a little larger or even smaller than the inner balloon member 30 when fully collapsed. In this way, the outer balloon 32 continues to contract as the inner balloon is deflated. Moreover, the resiliency of the outer balloon can assist in the process of collapsing the inner balloon member 30 and can also ensure that once fully deflated, the balloon assembly 20 is compact and does not have any loose parts which could snag as the catheter assembly is withdrawn from the patient.

FIG. 5 also shows the inner and outer balloon bonds 40, 42 which bond these elements to the catheter 12. Furthermore, this particular example of FIG. 5 shows an additional drug eluting port 46 in a wall of the catheter itself. This may be advantageous when it is desired to administer drug or other treatment fluid more generally in a particular part of a patient's vasculature or organ.

One or more radio opaque markers 48 may be provided on a suitable element of the balloon assembly 20 or of the catheter assembly. In some embodiments, the markers 48 are arranged to indicate the location of the holes 38.

The assembly allows for a guide wire 50 to pass therethrough. The holes 38, 46 might all be of the same size but could also be of different sizes as desired for any particular treatment.

It will be apparent that in the preferred embodiment there is very little dead space within the drug or other fluid delivery elements of the assembly. This reduces the amount of treatment fluid which is required and allows more accurate doses to be delivered. Moreover, the preferred embodiments can provide devices significantly smaller in diameter than prior art devices.

Figure 6:
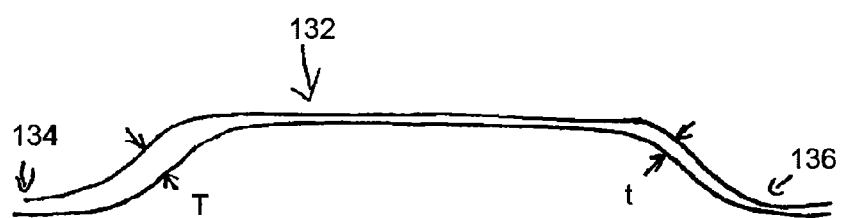
FIG. 6 shows a cross-sectional view of another embodiment of outer balloon member.

Referring now to FIG. 6, this is shown a cross-sectional view of a part of an embodiment of outer balloon member 132 in which the thickness of the wall of the member 132 can be seen. The left-hand side of the drawing represents the proximal end 134 of the balloon member 132 while the right-hand side of the drawing represents the distal end 136 of the member 132. In this embodiment, the thickness T of the wall of the balloon member 132 at the proximal end $\overline{1}34$ is greater than its thickness t at the distal end 132. In the particular embodiment shown, most of the wall of the member 132 has the smaller thickness t, with only the proximal end 134 being of the greater thickness T. It is, however, envisaged that the wall thickness could decrease gradually from the proximal to the distal end.

The purpose of the different wall thickness to the outer balloon member 132 is to improve or control the flow of bioactive material through the balloon assembly, and in particular to avoid accumulation of bioactive material at the proximal end of the balloon assembly resulting from the expansion of the proximal end of the outer balloon member as a result of its compliance. The skilled person will appreciate that this feature might only be appropriate in particular instances of balloon structure or size.

Although the embodiments described above provide an outer balloon member 32 which has holes therein for elution of treatment fluids, it is also envisaged that the outer balloon member 32 could be formed from a porous material.

The balloon catheter assembly taught herein can be used to deliver to a patient site any of the large range of treatment materials known in the art, including drugs, bioactive agents, therapeutic agents and diagnostic agents. As such materials are known in the art, they are not listed herein.

The invention claimed is:

1. A medical balloon assembly for administration of treatment material to a vessel or organ of a patient including an inner balloon member and an outer balloon member, the inner balloon member being located within the outer balloon member so as to be enveloped thereby, the outer balloon member being more compliant than the inner balloon member and being configured such that an interior surface of the outer balloon is biased so as to engage the inner balloon member along substantially an entire length of the outer balloon when the inner balloon member is in any of an uninflated state, a partially inflated state, or a fully inflated state, the outer balloon member being configured for the passage of fluids therethrough, wherein the outer balloon member has a resiliency operable to close off passage of a treatment fluid through the balloon assembly in the absence of a treatment fluid delivery pressure.

2. The medical balloon assembly according to claim 1, wherein the outer balloon member is provided with one or more holes or ports therein for elution of a treatment fluid.

3. The medical balloon assembly according to claim 1, wherein the outer balloon member is formed of a porous material.

4. The medical balloon assembly according to claim 1, wherein the inner balloon member is formed of a substantially non-compliant material.

5. The medical balloon assembly according to claim 1, wherein the inner and outer balloon members are made from the same material.

6. The medical balloon assembly according to claim 5, wherein the inner balloon member has a thicker balloon member wall relative to the outer balloon member.

7. The medical balloon assembly according to claim 1, wherein the wall of the outer balloon member is thicker at a proximal end thereof relative to a distal end thereof.

8. The medical balloon assembly according to claim 1, wherein there is provided a plurality of holes in the outer balloon member extending in a longitudinal direction along at least a portion thereof.

9. The medical balloon assembly according to claim 8, wherein the plurality of holes are arranged substantially symmetrically around a circumference of the outer balloon member.

10. The medical balloon assembly according to claim 8, wherein the plurality of holes are provided in a uniformly spaced pattern on the outer balloon member.

11. The medical balloon assembly according to claim 8, wherein the plurality of holes comprise different sizes.

12. The medical balloon assembly according to claim 1, including one or more radio-opaque markers.

13. The medical balloon assembly according to claim 12, wherein the markers are operable to identify a radial location of the balloon assembly.

14. A balloon catheter assembly including a medical balloon assembly according to claim 1 and a catheter element including a first lumen through which balloon inflation fluid can be supplied to the inner balloon member, and a second lumen through which a treatment fluid can be supplied between the inner and outer balloon members.

15. A method of treating a patient including the steps of:
providing a balloon catheter assembly including an elongate shaft, an inner balloon member and an outer balloon member, the inner balloon member being located within the outer balloon member so as to be enveloped thereby, the inner balloon having an overall length that is substantially equal to an overall length of the outer balloon, the inner balloon member being in fluid communication with an inflation lumen extending through the shaft, the outer balloon member being in fluid communication with a delivery lumen extending through the shaft, the outer balloon member being more compliant than the inner balloon member and being configured so as to be engaged and stretched by the inner balloon member when the inner balloon member is in an inflated state, the outer balloon member being configured for the passage of fluids therethrough;
inflating the inner balloon member by passing an inflation fluid through the inflation lumen; and
passing a treatment fluid through the delivery lumen to between the inner and outer balloon members to thereby cause said treatment fluid to open holes in the outer balloon member and to allow said treatment fluid to elute from the balloon assembly.

16. A medical balloon assembly for administration of treatment material to a vessel or organ of a patient including inner and outer balloon members, the inner balloon member being located within the outer balloon member so as to be enveloped thereby, the outer balloon member being more compliant than the inner balloon member and being of a size so as to be in a stretched condition along an entire length thereof when the inner balloon member is inflated, the outer balloon member allowing the passage of fluids therethrough;
wherein the wall of the outer balloon member comprises a wall thickness that is greater at a proximal end thereof relative to a distal end thereof;
wherein the outer balloon member has a resiliency operable to close off passage of treatment fluid through the balloon assembly in the absence of treatment fluid delivery pressure; and
wherein the inner balloon member is formed of a substantially non-compliant material.

* * * * *